United States Patent [19]

Sagusa et al.

[11] 4,263,512

[45] Apr. 21, 1981

[54] COLORIMETRIC METHOD FOR LIQUID SAMPLER INCLUDING DISTURBING CHROMOGENS

[75] Inventors: Hisayuki Sagusa, Katsuta; Yasushi Nonura, Mito; Ryohei Yabe, Katsuta, all of Japan

[73] Assignee: Hitachi, Ltd., Tokyo, Japan

[21] Appl. No.: 956,354

[22] Filed: Oct. 31, 1978

[30] Foreign Application Priority Data

Oct. 31, 1977 [JP] Japan .............................. 52-129602
Nov. 11, 1977 [JP] Japan .............................. 52-134600

[51] Int. Cl.³ .......................................... G01N 21/33
[52] U.S. Cl. ..................................... 250/373; 356/39; 356/51; 356/320; 356/407
[58] Field of Search .................. 356/39, 40, 320, 328, 356/407, 409, 414, 418, 419, 51; 250/373

[56] References Cited

U.S. PATENT DOCUMENTS

| | | | |
|---|---|---|---|
| 3,569,721 | 3/1971 | Goldberg et al. | 356/321 X |
| 3,833,304 | 9/1974 | Liston | 356/419 X |
| 3,893,770 | 7/1975 | Takami et al. | 356/328 |

OTHER PUBLICATIONS

Allen et al., *Analytical Chemistry*, vol. 25, No. 9, Sep. 1953, pp. 1325-1331.

*Primary Examiner*—F. L. Evans
*Attorney, Agent, or Firm*—Craig and Antonelli

[57] ABSTRACT

Color former is added to blood serum sample color it, and measurements for specific components are determined based on the light absorbance caused by coloring. For one sample, a differential light absorbance between two wavelengths at each of long wavelength region, middle wavelength region and short wavelength region within a visible wavelength band is determined. The degree of chyle is determined from the measurements for the long wavelength region, the degree of hemolysis is determined from the measurements for the middle wavelength region, and the degree of icterus is determined from the measurements for the short wavelength region. The measurements for the specific components are then corrected by the degree of chyle, degree of hemolysis and degree of icterus to obtain highly correct measurements.

12 Claims, 5 Drawing Figures

COLORIMETRIC METHOD FOR LIQUID SAMPLER INCLUDING DISTURBING CHROMOGENS

BACKGROUND OF THE INVENTION

The present invention relates to a colorimetric method, and more particularly to a colorimetric method suited to be applied in analyzing blood sample which has an influence by chyle, hemolysis and icterus.

A recent tendency of automation in the field of biochemistry is remarkable. Various types of automatic clinical analyzers including a flow type analyzer in early time and a discrete type analyzer in modern time have been developed. Those automatic clinical analyzers have made remarkable contribution in increasing total number of test items and improving precision of measurements. However, from the viewpoint of correctness of the measurements, the presently available automatic clinical analyzers still have some problems and they are far from the requirement of users. Among others, various chromogens such as hemolysis (hemoglobin), icterus (birilbin) and chyle (turbidity) cause the loss of exactness of the measurements by the automatic clinical analyzers.

The influence by the disturbing chromogens is particularly remarkable in colorimetric method and nephelometric method using endpoint method, and it is very little in a rate method (reaction rate measurement method). However, the utilization of the rate method to all materials to be tested biochemically is principally possible but problems exist in the prices of reagents, complexity of processing and processing speed. Accordingly, in present days, very high percentage of overall tests are made by the colorimetric method.

Accordingly, if a colorimetric method (including nephelometric method) which is free from the influence by the chromogens and provides high correctness is developed, it will play an important role to the automation of the analyzer.

One method which has been heretofore been considered to be most basic one to prevent the disturbance by those chromogens is to measure test sample blank for each test sample and test item. Although there are many problems to be discussed, such as composition of reagent, basically the test sample blank is measured using a reagent which does not include certain ones of materials which are relevant to the measurement reaction, and the test sample is determined from a difference between the measurement by that reagent and the measurement by reaction solution for the test sample. In this method, it is possible to obtain correct measurement of analysis which is close to the true value and free from the influence by the disturbing material. However, when such test sample blank correction method is used in the automatic clinical analyzer, two times of measurements are required for each sample and the processing speed of the analyzer necessarily reduced to one half and increased number of reagents are required. Accordingly, this method is presently not used except certain test for special items.

Another factor which causes the loss of exactness of the measurements in the colorimetric method is air bubbles and solids. These are observed both in the colorimetric method of flow cell type and in the direct colorimetric method using a test tube.

There are more than 40 sorts of materials to be measured by the colorimetric method in the biochemical test. Heretofore, a single wavelength method or a dual wavelength method has been used in the colorimetric method. The former measures a light absorbance at a particular wavelength near an absorbance center of a reacting material corresponding to the test sample or a reaction product, and the latter measures a difference between light absorbances at a wavelength near the absorbance center and an another appropriate wavelength. However, both methods are subjected to the influence by the disturbing chromogens.

SUMMARY OF THE INVENTION

It is an object of the present invention to provide a method for determining the influence to the measurements by the disturbing chromogens.

It is another object of the present invention to provide a method for determining the degree of chyle, degree of hemolysis and degree of icterus in a test sample.

It is another object of the present invention to provide an analyzing method which provides correct measurements free from the disturbance by the disturbing chromogens.

It is another object of the present invention to provide an analyzing method which does not result in the reduction of processing ability to the test sample even when a process for eliminating the influence by the disturbing components is performed.

According to one aspect of the present invention, light is radiated to a test sample which includes disturbing chromogens, and light absorbances at long wavelength, middle wavelength and short wavelength in a visible wavelength range are measured, and the degree of chyle is determined from the measurement at the long wavelength, the degree of hemolysis is determined from the measurements at the middle wavelength and the degree of icterus is determined from the measurements at the short wavelength.

According to another aspect of the present invention, color former appropriate for the composition of the saple is added to the sample to color the sample, and depending on the degree of color development, the light absorbances or difference of color absorbances are measured by the single wavelength method or the double wavelength method, and the resulting measurements are corrected by the degree of chyle, degree of hemolysis and degree of icterus determined for the same sample by the method described above to reduce the measurement error.

DETAILED DESCRIPTION OF THE PREFERRED EMBODIMENTS

Before explaining the preferred embodiment of the present invention, a relation between the disturbing components and the absorption spectra in the colorimetric method is first explained with reference to FIG. 1.

Figure 1:
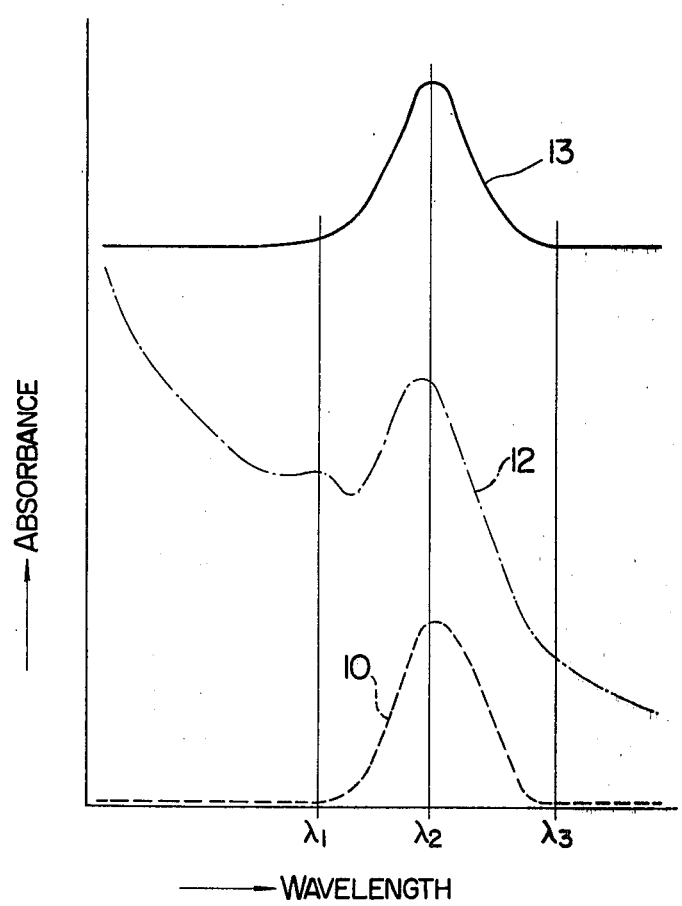
FIG. 1 shows a model chart of error factors in the colorimetric method.

In FIG. 1, a spectrum 10 shows an absorption spectrum for an ideal blood serum reactant which is free from disturbing material, and a spectrum 12 shows an absorption spectrum for an actual blood serum reactant which includes disturbing materials such as chyle, hemolysis and icterus. A spectrum 13 shows an absorption spectrum for the same reactant as that for the spectrum 10, with air bubbles or solids being mixed therewith. In FIG. 1, considering a single wavelength colorimetric method at a wavelength $\lambda_2$, the concentrations of the test component in those three test samples should be approximately same, but actually the measurements from the spectrum 12 are approximately two times as high as those from the spectrum 10 and the measurements from the spectrum 13 are approximately four times as high as those from the spectrum 10. When a double wavelength colorimetric method is used, the minute air bubbles or solids generally shift the spectra in parallel along the ordinate and the errors are not as large as the errors induced in the single wavelength colorimetric method. However, in the double wavelength colorimetric method, the disturbance by the chromogens is complex as shown by the spectrum 12, and when wavelengths $\lambda_2$ and $\lambda_3$ are used, a 50% positive error is induced, and when the wavelengths $\lambda_2$ and $\lambda_1$ are used, a 30% negative error is induced.

The absorption spectra for the disturbing chromogens such as the chyle, hemolysis and icterus which are often included in the actual blood serum change depending on liquid property and in many cases they overlap to each other. Therefore, the spectrum analysis thereof is difficult. Among others, when the absorption by the test sample is superimposed on those absorption spectra, the analysis thereof is more difficult, and even if it is possible, the precision is materially low. Therefore, where many items are to be simultaneously tested for the same test sample like in a multi-item automatic analyzer, it is easier to analyze a spectrum for an item which is most easy to analyze, determine the amounts of the three disturbing materials from the resulting spectrum and correct the measurements for other items using the determined amounts of the disturbing material, than to analyze a spectrum for each test item. The items which are most easy to analyze the disturbing chromogens are those items which are measured using ultraviolet absorption, such as glutamic acid-oxiaroacetic acid-transaminase (GOT), glutamic acid-pyrunic acid-transaminase (GPT), lactic acid-dehydroenzyme (LDH) or hydroxi-butylic acid-dehydroenzyme (HBDH). In the measurement of those test items, the light absorption of the test sample, that is, nicotine amidadenine denucleotid (NADH) occurs only in the ultraviolet region, and in the visible wavelength region, it does not overlap the absorption spectrum of the disturbing materials. Furthermore, since the reagent does not include material which reacts with hemoglobin, icterus or lipoprotein (one cause of turbidity) and it is a neutral buffer liquid (ph 7.4), the spectra for the disturbing materials are relatively simple in their shapes and hence they are easy to analyze.

Figure 2:
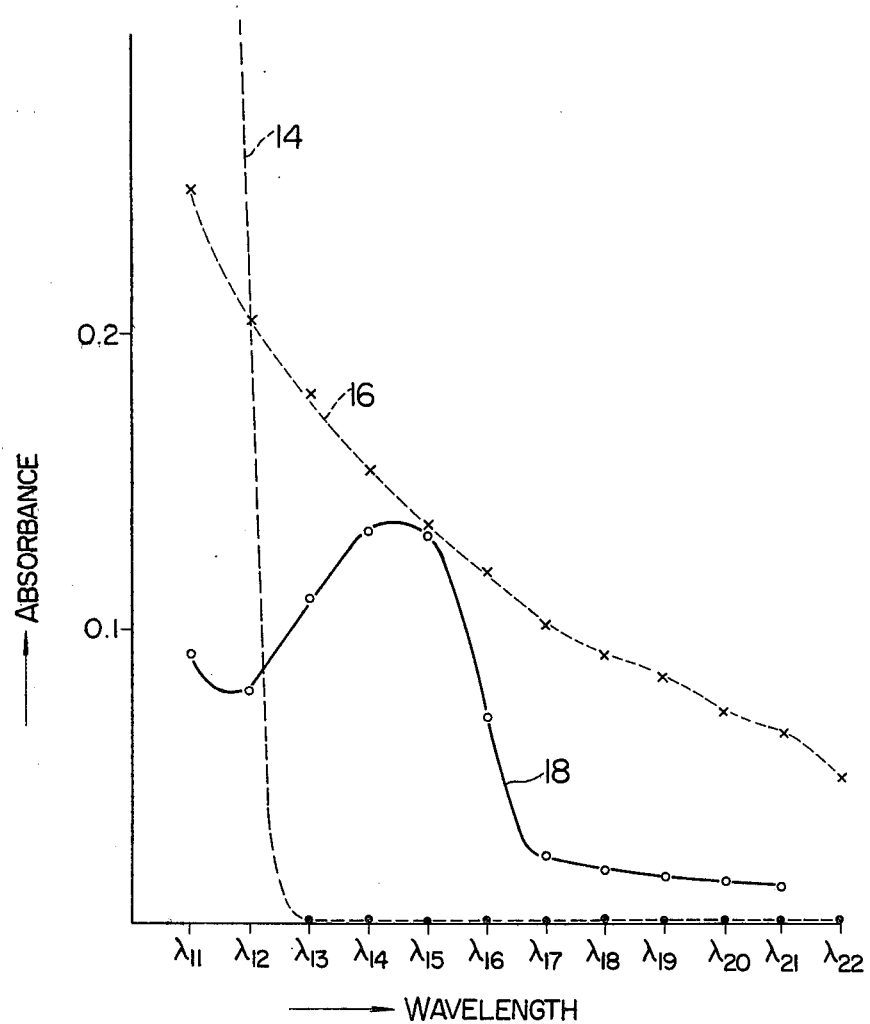
FIG. 2 shows typical blood serum absorption spectra in a visible wavelength range in a GOT reaction.

FIG. 2 shows absorption spectra in the visible wavelength region for the ultraviolet measurement of a typical blood serum by GOT reaction. In FIG. 2, a curve 14 shows an NADH absorption spectrum, in contrast to water, of an ideal normal blood serum which is completely free from the disturbing chromogens, a curve 16 shows an absorption spectrum, in contrast to reagent blank, of a blood serum reactant including high density of chyle, and a curve 18 shows an absorption spectrum, in contrast with reagent blank, of a blood serum reactant including high density of icterus. Wavelength $\lambda_{11}$ is 340 nm, $\lambda_{12}$ is 376 nm, $\lambda_{13}$ is 415 nm, $\lambda_{14}$ is 450 nm, $\lambda_{15}$ is 480 nm, $\lambda_{16}$ is 505 nm, $\lambda_{17}$ is 546 nm, $\lambda_{18}$ is 570 nm, $\lambda_{19}$ is 600 nm, $\lambda_{20}$ is 660 nm, $\lambda_{21}$ is 700 nm and $\lambda_{22}$ is 850 nm. By analyzing the spectra of the reactant in the visible wavelength region in the GOT measurement, the amounts of the disturbing chromogens can be determined.

Figure 3:
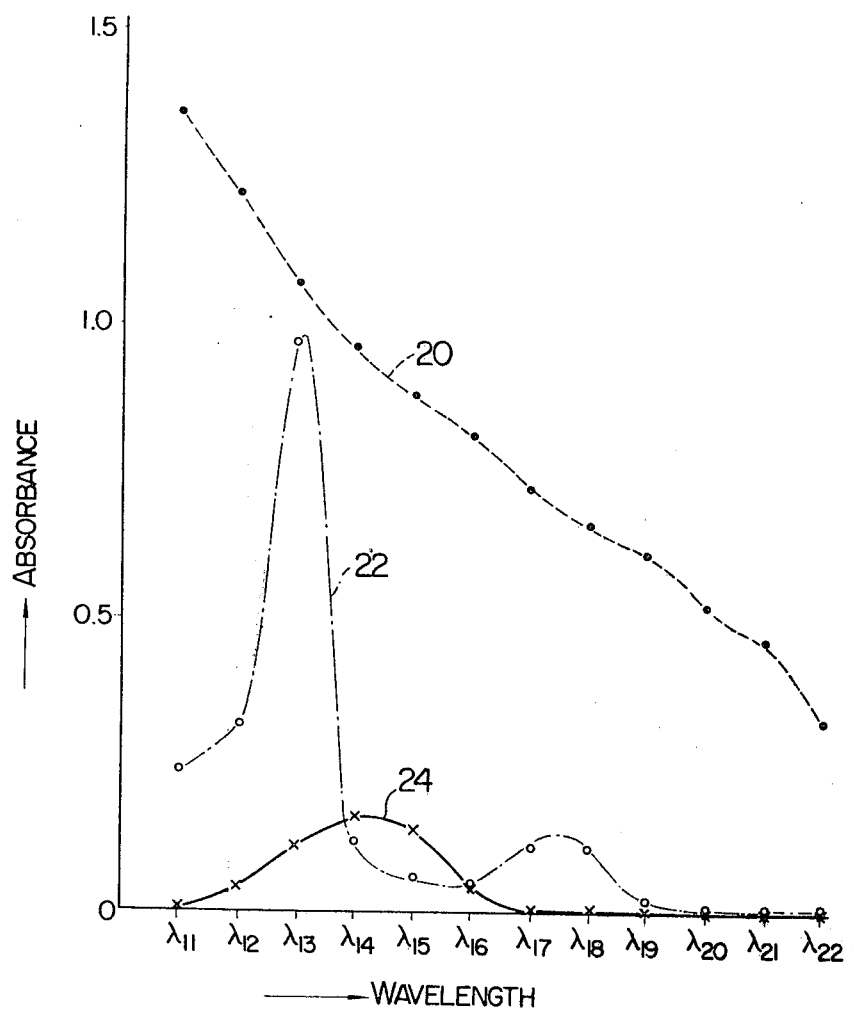
FIG. 3 shows reference spectra for chyle, hemolysis and icterus in the GOT reaction.

One embodiment of the present invention, which uses a multi-wavelength automatic analyzer using 12 wavelengths as measuring wavelength is now explained in detail. FIG. 3 shows absorption spectra of the disturbing components obtained by the multi-wavelength automatic analyzer. A curve 20 shows a spectrum for a reference chyle liquid diluted with GOT measuring liquid, a curve 22 shows a spectrum for a reference hemolysis liquid diluted with GOT measuring liquid, and a curve 24 shows a spectrum for a reference icterus liquid diluted with GOT measuring liquid. The reference chyle liquid is prepared by diluting and emulsing fine polystylene grains in the order of 20 Kunkel unit with GOT reagent, the reference hemolysis liquid is prepared by diluting and dissolving reference hemoglobin liquid of 1000 mg/dl with GOT measuring liquid at the same condition as the blood serum under test, and the reference icterus liquid is prepared by diluting and dissolving birilbin control blood serum of 10 mg/dl with GOT measuring liquid at the same condition as the blood serum under test. The spectra 20, 22 and 24 are depicted in contrast to reagent blank. The wavelengths used are same as those in FIG. 2.

It is seen from FIG. 3 that of the test sample blank absorption appearing in the visible wavelength region within the width of GOT reagent, the absorption in a long wavelength region ($\lambda_{20}$–$\lambda_{22}$) is due to chyle, the absorption in a middle wavelength region ($\lambda_{17}$–$\lambda_{19}$) in due to chyle and heomlysis, and the absorption in a short wavelength region ($\lambda_{11}$–$\lambda_{16}$) is due to the three components, chyle, hemolysis and icterus. Thus, those three components can be separately discriminated in the following manner.

The absorption spectra for the test sample reactant in GOT measurement are measured over the entire wavelength region by the multi-wavelength spectrometer and the GOT of the test sample is determined by the ultraviolet absorption. At the same time, the degrees of chyle, hemolysis and icterus in the test sample blood serum are determined by the visible wavelength spectra in the following manner.

The degree of chyle X is determined from a difference between light absorbances at two wavelengths (e.g. $\lambda_{20}$ and $\lambda_{21}$) which lie between $\lambda_{20}$ and $\lambda_{22}$. That is;

$$X = \frac{A_{20-21}}{T_{20-21}} \qquad (1.)$$

where $A_{20-21}$ is the difference between light absorbances of the test sample at the wavelengths $\lambda_{20}$ and $\lambda_{21}$, and $T_{20-21}$ is a constant indicative of a differential light absorbance per unit degree of turbidity determined from the spectrum 20.

The degree of hemolysis Y is determined from a differential light absorbance $A_{18-19}$ for two wavelengths (e.g. $\lambda_{18}$ and $\lambda_{19}$) in the middle wavelength region. That is;

$$Y = \frac{A_{18-19} - X \cdot T_{18-19}}{H_{18-19}} \quad (2)$$

where $T_{18-19}$ is a constant indicative of a differential light absorbance per unit degree of turbidity determined from the spectrum 20, and $H_{18-19}$ is a constant indicative of a differential light absorbance per unit degree of hemolysis determined from the spectrum 22.

The degree of icterus Z is determined from a differential light absorbance $A_{15-16}$ for two wavelengths (e.g. $\lambda_{15}$ and $\lambda_{16}$) in the short wavelength region. That is;

$$Z = \frac{A_{15-16} - X \cdot T_{15-16} - Y \cdot H_{15-16}}{B_{15-16}} \quad (3)$$

where $T_{15-16}$ is a constant indicative of a differential light absorbance per unit degree of turbidity determined from the spectrum 20, $H_{15-16}$ is a constant indicative of a differential light absorbance per unit degree of hemolysis determined from the spectrum 22, and $B_{15-16}$ is a constant indicative of a differential light absorbance per unit degree of icterus determined from the spectrum 24.

Using the degree of chyle X, degree of hemolysis Y and degree of icterus Z determined above, the measurements S obtained from the colorimetric method are corrected using the following formula to obtain more correct measurements S'.

$$S' = S - \alpha \cdot X - \beta \cdot Y - \gamma \cdot Z \quad (4)$$

where $\alpha$, $\beta$ and $\gamma$ are coefficients determined by measuring the reference chyle, hemoylsis and icterus liquids under the same measurement conditions as those for the test sample.

The constant $T_{20-21}$, $T_{18-19}$, $T_{15-16}$, $H_{18-19}$, $H_{15-16}$, $B_{15-16}$, $\alpha$, $\beta$ and $\gamma$ used in the above formulas are constant for a given analyzer and a given reagent. Therefore, once they are determined, they need not be determined for each run.

The effect of the correction is shown in Table 1. The analyzer used is an automatic analyzer capable of processing 16 test items at a speed of 120 items/hour and it has a multi-wavelength spectrometer capable of measuring the absorbance at 12 wavelengths ranging from 340 nm to 850 nm as shown in FIG. 3.

TABLE 1

| Item | Dual Wavelength Measurements | Correction Value | |
|---|---|---|---|
| CHE | −0.14 (ΔpH) | 0.49 (ΔpH) | X = 0.4 (Kunkel unit) |
| ALP | 1.93 (K.A. Unit) | 12.1 (K.A. Unit) | Y = 950 (mg/dl) (hemoglobin) |
| LAP | 137 (Takahashi Unit) | 55 (Takahashi Unit) | Z = 0.85 (mg/dl) (Birilbin) |
| TG | −15 (mg/dl) | 97 (mg/dl) | |

In Table 1, choline esterase (CHE) was measured by 570–600 nm dual wavelength colorimetric method, alkali phosphatase was by 546–600 nm, leucine aminopeptitase (LAP) was by 480–505 nm, triglycelide (TG) was by 340–376 nm. The test sample blood serum included high density of hemolysis as seen from the measurements of the degree of chyle X, degree of hemolysis Y and degree of icterus Z. As seen from Table 1, the measurements from the dual wavelength colorimetric method, which include non-theoretical negative value measurements for CHE and T.G. due to the disturbance by high density of hemolysis, are corrected using the degree of chyle X, degree of hemolysis Y and degree of icterus Z, determined from the spectra for the same test sample measured by GOT measurement.

In the present embodiment, the degree of chyle which is one of the disturbing chromogens in the test sample is determined from the difference between the light absorbances at two wavelengths in the long wavelength region of the visible wavelength absorbance spectra, the degree of hemolysis is determined from the degree of chyle and the difference the light absorbances at two wavelengths in the middle wavelength region, and the degree of icterus is determined from the degree of chyle, the degree of hemolysis and the difference between the light absorbances at two wavelengths in the short wavelength region. Accordingly, the degrees of the respective disturbing chromogens can be separately and precisely determined.

While the spectrum for the GOT measuring liquid is used in the above embodiment to determine the amounts of the disturbing chromogens, spectra for ultraviolet measurement liquids such as GPT, LDH or HBDH may be used to determine the amounts of the disturbing chromogens.

Furthermore, while the above embodiment shows the application of the dual wavelength colorimetric method to the present invention, the present invention may be applicable to a single wavelength colorimetric method which uses the absorbance at a single appropriate wavelength.

An arrangement of an automatic clinical analyzer embodying the present invention is now explained with reference to FIG. 4.

Figure 4:
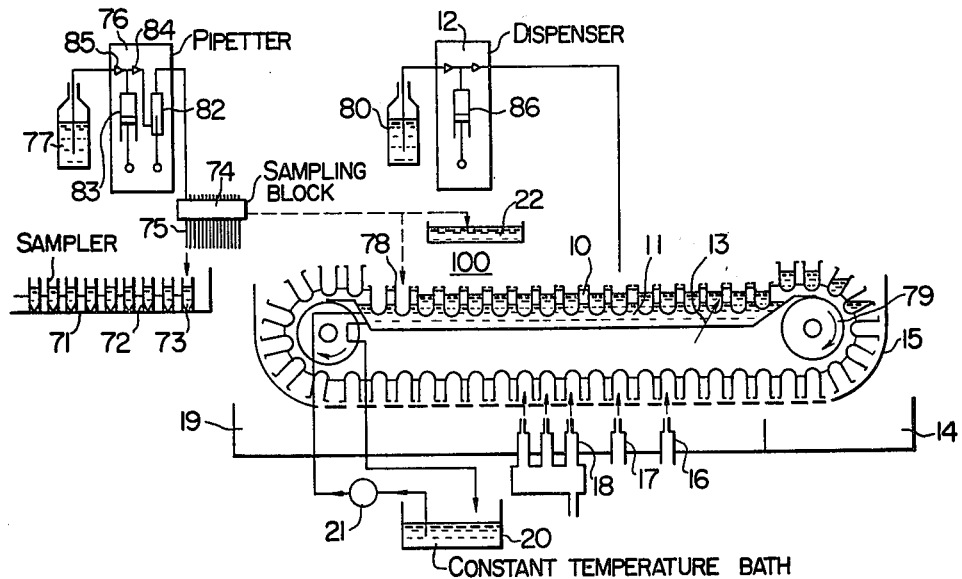
FIG. 4 shows a schematic diagram of an analyzer to which the present invention has been applied.

In FIG. 4, a sampler 71 has a tray on which a row of sample cups 72 are mounted. The row of sample cups are transported through a passage formed on the tray. In the course of the passage, a sample suction station is provided. A chain which accommodates the sample cups is stepped by a distance corresponding to a pitch of the sample cups. Therefore, the sample cups sequentially pass through the sample suction station.

Sample 73 in each of the sample cups 72 arranged on the sampler 71 is sucked at the sample suction station into a sample suction tube 75 which is attached to a sampling block 74, and it is held at a tip end of the sample suction tube 75. The sampling block 74 is movable horizontally. Two such sampling blocks are provided, each having six sample suction tubes 75.

Each of the sample suction tubes 75 corresponds to different one of test items. For example, when three test items are needed for a particulate sample, three sample suction tubes are sequentially inserted, one at a time, into the sample cup which accommodates that sample. Each sample suction tube 75 is connected to a microsyringe 82 of a pipetter 76, which includes the microsyringe 82, a syringe 83, a valve 84, a valve 85 and a reagent bottle 77. In order to suck the sample in the sample cup 72 into the sample suction tube 75, a piston of the microsyringe 82 is dropped. At this time, the valve 84 is kept closed and the valve 85 is kept open. At the same time, a piston of the syringe 83 is dropped so that reagent in the reagent bottle 77 is sucked into the syringe 83. The type of reagent changes depending on the test items.

After sample has been held in the sample suction tubes which correspond in number to the number of items to be tested for that sample, the sampling block 74 is moved on a reaction line 100. Empty reaction containers 78 are sequentially transported to a discharge station on the reaction line. The sample in one sample suction tube 75 is discharged into one reaction container and then the reagent from the same suction tube is discharged into that reaction container. Then, the reaction container is stepped and a next empty reaction container 78 comes to the discharge station. The sample in the second sample suction tube and the reagent for the desired test item are discharged into the second reaction container. After the sample in all of the sample suction tubes for the desired test items has been discharged, the suction tubes 75 are cleaned a cleaning bath 22.

When the sample is discharged into the reaction container 78, the valve 85 of the pipetter 76 is closed while the valve 84 is opened. Both the piston of the microsyringe 82 and the piston of the syringe 83 rise to drive out the liquids in the respective syringe toward the suction tube 75. As a result, the sample held at the end of the suction tube 75 is discharged and then the reagent is discharged.

After the sample suction tubes 75 have been cleaned, the block 74 is moved to the sample suction station of the sampler 71. The sample cup which contain the next sample has been arrived at the sample suction station. The similar operation is thereafter repeated.

In the reaction line 100, an endless chain 10 is intermittently moved. A number of reaction containers 78 are vertically slidably loaded to the endless chain 10. The reaction container 78 which contain sample are transported while they are immersed in a constant temperature water bath 11. The reaction containers 78 are intermittently moved in the constant temperature water bath 11 by the endless chain 10 which is driven by sprocket wheels 79. Reagent necessary for the reaction is added into the reaction containers by a dispensor 12 at an appropriate position on the reaction line 100. When the sample which has reacted in the reaction container 78 reaches a measurement station 13, a light absorbance of the reacted sample is measured in a method to be described later. The reacted sample having been measured is further moved out of the constant temperature water bath 11 and the reaction container is inverted at the end of the reaction line 100 to discharge the content. The discharged sample drops into an exhaust sample tank 14 and thence it is guided to an appropriate storage tank (not shown). The reaction container 78 is further moved along a guide 15 and subjected to tap water rinsing by a nozzle 16 and distilled water rinsing by a nozzle 17 and hot air drying by a nozzle 18 and then again inverted to a normal position and moved to the sample discharging station for reuse. The exhausted rinsing liquid drops down the guide 15 and is collected at a rinsing liquid exhaust tank 19, thence it is exhausted via an exhaust tube (not shown). Water in the constant temperature water bath 11 is circulated through a constant temperature bath 20.

Figure 5:
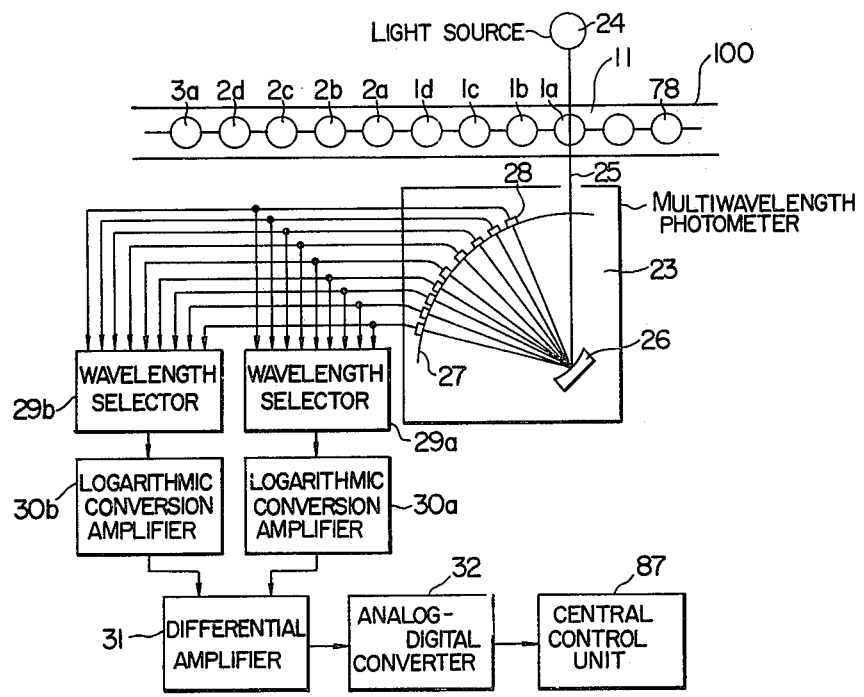
FIG. 5 shows a photosensitive unit of the analyzer of FIG. 4.

FIG. 5 illustrates the photomeasurement unit in FIG. 4. A series of samples $1a-1d, 2a-2d, 3a\ldots$ contained in the reaction containers 78 are arranged on the reaction line 100. In the illustrated embodiment, the line of reaction containers 78 are moved intermittently and the reacted sample $1a$ arrives a position through which a light beam 25 from a light source 24 passes, and stops there momentarily. At this time, the light beam 25 is subjected to light absorption by the reacted sample $1a$. The light beam 25 is directed to a concave diffraction grating 26 of a multi-wavelength photometer 23 where it is dispersed into spectra and the light beams of the respective wavelengths are collected on a Rowland circle 27. A plurality of sensors 28 capable of at least the wavelengths shown in FIGS. 2 and 3 are arranged on the Rowland circle 27. Outputs from the sensors 28 are applied to two wavelength selectors 29a and 29b to measure the wavelength. They select the signals from the sensor which sensed the wavelength corresponding to the test item a and supply those signals to logarithmic conversion amplifiers 30a and 30b. A differential amplifier 31 produces a difference between outputs of the two logarithmic conversion amplifiers 30a and 30b and supplies it to an analog-digital converter 32, an output of which is supplied to a central control unit 87 where it is arithmetically processed.

After the measurement for the sample $1a$ has been completed, the reaction container 78 for the next sample $1b$ is moved to the light beam position, where the sample $1b$ is measured in the same manner. The two measuring wavelengths are selected in accordance with the test item b by the wavelength selectors 29a and 29b.

In measuring the sample, after the wavelength selectors 29a and 29b have selected two wavelengths to obtain information on the test item, they further select pairs of wavelengths in the long wavelength region, middle wavelength region and short wavelength region in the visible wavelength band sequentially. The light absorbance information for those pairs of wavelengths is also supplied to the central control unit 87 to carry out necessary arithmetic operation. The result of the arithmetic operation is printed out by a printer, not shown. That is, the densities of the test items which have been compensated for the influence by chyle, hemolysis and icterus are printed out. The degrees of chyle, hemolysis and icterus are also printed out together with the resulting measurements.

Another embodiment of the present invention is now explained. In the present embodiment, the colorimetric analysis is made for one sample by both the single wavelength colorimetric method and the dual wavelength colorimetric method, and if a ratio of the resulting measurements by both method is within a predetermined range close to 1, the measurements are used as final measurements, and if the ratio is not within the predetermined range, the measurements by both methods are corrected in accordance with the amount of disturbing components included in the sample. If a ratio of the corrected measurements is within a predetermined range close to 1, the corrected measurements are used as final measurements, and if the ratio is not within the predetermined range, corrected measurements by the dual wavelength colorimetric method are used as final measurements, or a request for retest or alarm is issued.

The present invention utilizes the fact that the measurements by the single wavelength method and the dual wavelength method are true only for an ideal test sample which is free from disturbing material, air bubbles and solids and the measurements by both methods are identical, while the measurements by both methods are not identical when the test sample includes the disturbing material, air bubbles or solids.

The present embodiment is explained in detail for an example in which six items A–F are simultaneously tested. The colorimetric analysis is carried out by reacting the sample in the same manner as in a conventional multi-item automatic analyzer, by both the single wavelength method and the dual wavelength method, and a ratio of the measurements by both methods is determined. When the measurements for the test items A-F by the single wavelength colorimetric method are given by $a_1$-$f_1$ and those by the dual wavelength colorimetric method are given by $a_2$-$f_2$, ratios $K_A$-$K_F$ thereof are given by the following formulas:

$$K_A = a_1/a_2 \tag{5}$$

$$K_B = b_1/b_2 \tag{6}$$

$$K_C = c_1/c_2 \tag{7}$$

$$K_D = d_1/d_2 \tag{8}$$

$$K_E = e_1/e_2 \tag{9}$$

$$K_F = f_1/f_2 \tag{10}$$

If the ratios $K_A$-$K_F$ determined in accordance with the above formulas are within a predetermined range close to 1, e.g. between 0.95 and 1.05, the measurements by one of the methods or mean value of both measurements are used as final measurements. In the above analysis, the degree of chyle X, the degree of hemolysis Y and the degree of icterus Z, which are the disturbing material in the blood serum test sample, are determined from a spectrum of a test item which is easiest to spectrum-analyze.

If any of the ratios $K_A$-$K_F$ is not within the predetermined range, the corresponding measurements are corrected using the degree of chyle X, degree of hemolysis Y and degree of icterus Z. For example, if the ratio $K_C$ is not within the predetermined range, corrected measurements $C_1'$ and $C_2'$ are determined by the following formulas (11) and (12):

$$C_1' = C_1 - \alpha X - \beta Y - \gamma Z \tag{11}$$

$$C_2' = C_2 - \alpha' X - \beta' Y - \gamma' Z \tag{12}$$

where $\alpha, \alpha', \beta, \beta', \gamma$ and $\gamma'$ are constants predetermined by the reagents used and the analyzer used. Then, a ratio $K_C'$ of the corrected measurements $C_1'$ and $C_2'$ is determined from;

$$K_C' = C_1'/C_2' \tag{13}$$

If the ratio $K_C'$ is within a predetermined range close to 1, e.g. between 0.95 and 1.05, the measurements $C_1'$, $C_2'$ or mean value of them are used as the final measurements for the test item C for the blood serum test sample.

If the ratio $K_C'$ of the corrected measurements determined by the formula (13) is not within the predetermined range after the correction by the formulas (11) and (12), there is a possibility that the air bubbles or solids such as dust exist in the test sample. Therefore, the measurements $a_2$-$f_2$ by the dual wavelength colorimetric method, which are considered to be relatively reliable, are tentatively used as the final measurements, but at the same time retest is requested.

In this manner, by measuring the degree of chyle, degree of hemolysis and degree of icterus for each test sample and processing the measurements with those data, the correctness of the colorimetric method is materially improved. Furthermore, since the air bubbles and the solids as dust can be discriminated, the reliability of the measurements is very high.

While the predetermined range of 0.95-1.05 is used for the ratio of the measurement in the above embodiment, this range is not restrictive and any other range may be used.

We claim:

1. Colorimetric method for liquid samples including disturbing chromogens, using a spectrometer capable of extracting a monochromatic light from ultraviolet and visible wavelength bands, which comprises the steps of:

obtaining a liquid sample including a reaction product with regard to a test item and disturbing chromogens, in which the light absorption of the liquid sample, aside from the light absorption by said disturbing chromogens, occurs in the ultraviolet wavelength band and not substantially in the visible wavelength band;

radiating light to said liquid sample, detecting intensity of transmission light on the basis of a monochromatic light absorbed at a long wavelength region of the visible wavelength band in which the absorption is due to chyle without substantially any absorption due to hemolysis or icterus, a monochromatic light absorbed at a middle wavelength region of the visible wavelength band in which the absorption is due to chyle and hemolysis without substantially any absorption due to icterus, and a monochromatic light absorbed at a short wavelength region of the visible wavelength band in which the absorption is due to hemolysis, icterus and chyle, and obtaining absorbances corresponding to said intensity of transmission light of said respective monochromatic lights;

determining degree of chyle of said liquid sample from the absorbance in the long wavelength region;

determining degree of hemolysis of said liquid sample from a value obtained by correcting the absorbance in the middle wavelength region by the degree of chyle;

determining degree of icterus of said liquid sample from a value obtained by correcting the absorbance in the short wavelength band by the degree of chyle and the degree of hemolysis;

measuring absorbance of said liquid sample at a suitable wavelength of said ultraviolet wavelength band so as to determine a measured value of said reaction product with regard to the test item; and correcting said measured value of said test item by the degree of chyle, the degree of hemolysis and the degree of icterus so as to determine a corrected value.

2. Colorimetric method according to claim 1, wherein each of said absorbances corresponding to said respective measuring wavelengths is equal to the difference between two absorbances measured at two wavelengths which are close to each other in the same wavelength region.

3. Colorimetric method according to claim 1 or 2, wherein the liquid sample including a reaction product with regard to a test item and disturbing chromogens is a product of a blood sample reacted with regard to said test item.

4. Colorimetric method for liquid samples of a source liquid including disturbing chromogens, using a spectrometer capable of extracting a monochromatic light from ultraviolet and visible wavelength bands, which comprises the steps of:

obtaining a first liquid sample which is the product of said source liquid reacted with regard to a first test item, said first liquid sample including disturbing chromogenes;

obtaining a second liquid sample which is the product of said source liquid reacted with regard to a second test item, said second liquid sample containing disturbing chromogens, wherein the light absorption of said second liquid sample, apart from the absorption due to the disturbing chromogens, occurs in the ultraviolet wavelength band and not substantially in the visible wavelength band;

radiating light to said second liquid sample, detecting the intensity of transmission light on the basis of a monochromatic light absorbed at a long wavelength region of the visible wavelength band in which the absorption is due to chyle without substantially any absorption due to hemolysis or icterus, a monochromatic light absorbed at a middle wavelength region of the visible wavelength band in which the absorption is due to chyle and heomolysis without substantially any absorption due to icterus, and a monochromatic light absorbed at a short wavelength region of the visible wavelength band in which the absorption is due to hemolysis, icterus and chyle;

determining absorbances of said second liquid sample corresponding to said monochromatic lights;

determining degree of chyle of said second liquid sample from the absorbance in the long wavelength region;

determining degree of hemolysis of said second liquid sample from a value obtained by correcting the absorbance in the middle wavelength region by the degree of chyle;

determining degree of icterus of said second liquid sample from a value obtained by correcting the absorbance in the short wavelength band by the degree of chyle and the degree of hemolysis;

measuring an absorbance of said first liquid sample at a suitable wavelength with regard to said first test item; and correcting said absorbance of said first liquid sample by the degree of chyle, the degree of hemolysis and the degree of icterus determined by said second liquid sample so as to determine a corrected value.

5. Colorimetric method according to claim 4, wherein each of said absorbances corresponding to said respective wavelengths is equal to the difference between two absorbances measured at two wavelengths which are close to each other in the same wavelength region.

6. Colorimetric method according to claim 4 or 5, wherein said source liquid is a blood sample.

7. Colorimetric method for liquid samples of a source liquid including disturbing chromogens using a spectrometer capable of extracting a monochromatic light from ultraviolet and visible wavelength bands, which comprises the steps of:

obtaining a first liqud sample which is the product of said source liquid reacted with regard to a first test item, said first liquid sample including disturbing chromogens;

obtaining a second liquid sample which is the product of said source liquid reacted with regard to a second test item, said second liquid sample including disturbing chromogens, wherein the light absorption of said second liquid sample, apart from the absorption due to the disturbing chromogens, occurs in the ultraviolet wavelength band and not substantially in the visible wavelength band;

radiating light to said second liquid sample, detecting the intensity of transmission light on the basis of a monochromatic light absorbed at a long wavelength region of the visible wavelength band in which the absorption is due to chyle without substantially any absorption due to hemolysis or icterus, a monochromatic light absorbed at middle wavelength region of the visible wavelength band in which the absorption is due to chyle and hemolysis without substantially any absorption due to icterus, and a monochromatic light absorbed at short wavelength region of the visible wavelength band in which the absorption is due to hemolysis, icterus and chyle;

determining absorbances of said second liquid sample corresponding to said monochromatic lights;

determining degree of chyle of said second liquid sample from the absorbance in the long wavelength region;

determining degree of hemolysis of said second liquid sample from a value obtained by correcting the absorbances in the middle wavelength region by the degree of chyle;

determining degree of icterus of said second liquid sample from a value obtained by correcting the absorbance in the short wavelength band by the degree of chyle and the degree of hemolysis;

measuring an absorbance of said second liquid sample at a suitable wavelength of the ultraviolet wavelength band with regard to said second test item;

correcting said absorbance of said second liquid sample by the degree of chyle, the degree of hemolysis and the degree of icterus so as to determine a corrected value;

measuring an absorbance of said first liquid sample at a suitable wavelength with regard to said first test item; and correcting said absorbance of said first liquid sample by said degree of chyle, the degree of hemolysis and the degree of icterus determined by said second liquid sample so as to determine a corrected value.

8. Colorimetric method according to claim 7, wherein each of said absorbances corresponding to said respective wavelengths is equal to the difference between two absorbances measured at two wavelengths which are close to each other in the same wavelength region.

9. Colorimetric method according to claim 7 or 8, wherein the source liquid is a blood sample.

10. Colorimetric method for liquid samples of a source liquid including disturbing chromogens, comprising the steps of:

obtaining a liquid sample which is a reaction product of the source liquid reacted with regard to a test item, wherein the liquid sample includes disturbing chromogens, the light absorption of the liquid sample including disturbing chromogens, apart from the light absorption due to the disturbing chromogens, occurring in the ultraviolet wavelength band and not substantially in the visible wavelength band;

radiating light to said liquid sample, detecting the intensity of transmission light on the basis of a monochromatic light absorbed at a long wavelength region of the visible wavelength band in which the absorption is due to chyle without substantially any absorption due to hemolysis or icterus, a monochromatic light absorbed at a middle wavelength region of the visible wavelength band in which the absorption is due to chyle and hemolysis without substantially any absorption due to icterus, and a monochromatic light absorbed at a short wavelength region of the visible wavelength band in which the absorption is due to hemolysis, icterus and chyle, and obtaining absorbances corresponding to said intensity of transmission light of said respective monochromatic lights;

determining degree of chyle of said liquid sample from the absorbance in the long wavelength region;

determining degree of hemolysis of said liquid sample from a value obtained by correcting the absorbance in the middle wavelength region by the degree of chyle;

determining the degree of icterus of said liquid sample from a value obtained by correcting the absorbance in the short wavelength band by the degree of chyle and the degree of hemolysis;

radiating light to said liquid sample, measuring two absorbances corresponding to two specific wavelengths relating to said test item, determining a first measured value for the test item on the basis of the absorbance corresponding to one of said specific wavelengths, and determining a second measured value for the test item on the basis of a difference between said absorbances corresponding to said two specific wavelengths; and comparing said first measured value with said second measured value and correcting at least one of said first and second measured values by the degree of chyle, the degree of hemolysis and the degree of icterus so as to determine a corrected value, when a value obtained by the comparison is outside a predetermined range.

11. Colorimetric method according to claim 10, wherein the source liquid is a blood sample.

12. Colorimetric method for determining the degree of disturbing chromogens in a source liquid comprising a test substance, comprising the steps of:

obtaining a sample liquid from said source liquid, which sample liquid is a reaction product of the source liquid reacted with regard to the test substance such that the absorbance of the sample liquid, apart from the light absorption due to said disturbing chromogens, occurs in the ultraviolet wavelength band and not substantially in the visible wavelength band;

radiating light to said liquid sample, detecting intensity of transmission light on the basis of a monochromatic light absorbed at a long wavelength region of the visible wavelength band in which the absorption is due to chyle without substantially any absorption due to hemolysis or icterus, a monochromatic light absorbed at a middle wavelength region of the visible wavelength band in which the absorption is due to chyle and hemolysis without substantially any absorption due to icterus, and a monochromatic light absorbed at a short wavelength region of the visible wavelength band in which the absorption is due to hemolysis, icterus and chyle, and obtaining absorbances corresponding to said intensity of transmission light of said respective monochromatic lights;

determining degree of chyle of said liquid sample from the absorbance in the long wavelength region;

determinining degree of hemolysis of said liquid sample from a value obtained by correcting the absorbance in the middle wavelength region by the degree of chyle; and determining degree of icterus of said liquid sample from a value obtained by correcting the absorbance in the short wavelength band by the degree of chyle and the degree of hemolysis.

* * * * *